United States Patent
Lott et al.

(10) Patent No.: US 10,031,108 B2
(45) Date of Patent: Jul. 24, 2018

(54) MULTI-FREQUENCY EDDY CURRENT PIPELINE INSPECTION APPARATUS AND METHOD

(71) Applicant: Exxam Systems, LLC, Anchorage, AK (US)

(72) Inventors: Paul Lott, Anchorage, AK (US); Yuan Ji, Anchorage, AK (US); John R. Bowler, Ames, IA (US)

(73) Assignees: Paul W. Lott, Anchorage, AK (US); Exxam Systems, LLC, Anchorage, AK (US)

( * ) Notice: Subject to any disclaimer, the term of this patent is extended or adjusted under 35 U.S.C. 154(b) by 0 days.

(21) Appl. No.: 14/878,736

(22) Filed: Oct. 8, 2015

(65) Prior Publication Data

US 2016/0103099 A1    Apr. 14, 2016

Related U.S. Application Data

(60) Provisional application No. 62/062,599, filed on Oct. 10, 2014.

(51) Int. Cl.
*G01N 27/90* (2006.01)

(52) U.S. Cl.
CPC ......... *G01N 27/904* (2013.01); *G01N 27/902* (2013.01)

(58) Field of Classification Search
CPC ........................... G01N 27/902; G01N 27/904
See application file for complete search history.

(56) References Cited

U.S. PATENT DOCUMENTS

| | | | | |
|---|---|---|---|---|
| 3,135,914 A | * | 6/1964 | Callan | G01N 27/9046 324/227 |
| 5,119,023 A | * | 6/1992 | Lloyd | G01N 27/9046 324/220 |

(Continued)

FOREIGN PATENT DOCUMENTS

| JP | 4998821 B2 | 8/2013 |
|---|---|---|
| WO | 2007064677 A1 | 6/2007 |

OTHER PUBLICATIONS

International Search Report & Written Opinion received for counterpart International Application No. PCT/US2015/054735; dated Jan. 15, 2016; (15 pages).

(Continued)

*Primary Examiner* — Jay Patidar
(74) *Attorney, Agent, or Firm* — Paul W. Lott; Exxam Systems LLC

(57) ABSTRACT

Apparatuses and methods for inspecting a section of piping are disclosed. In one example embodiment, an apparatus includes first and second excitation coils, a plurality of magnetometers, and a data acquisition system. The first excitation coils are disposed at a first axial location and are energized and the second excitation coils are disposed at a second axial location and are energized. The plurality of magnetometers are disposed at an axial location between the first and second axial locations and are positioned to detect magnetic fields generated by eddy currents induced in the section of piping by the first and second excitation coils. The data acquisition system is operatively connected to receive output data from the plurality of magnetometers.

22 Claims, 12 Drawing Sheets

(56) References Cited

U.S. PATENT DOCUMENTS

| | | | | |
|---|---|---|---|---|
| 5,237,271 A | * | 8/1993 | Hedengren | G01N 27/9046 |
| | | | | 324/232 |
| 5,329,561 A | * | 7/1994 | Desruelles | G01B 17/025 |
| | | | | 324/226 |
| 5,446,382 A | * | 8/1995 | Flora | G01N 27/902 |
| | | | | 324/232 |
| 5,793,205 A | * | 8/1998 | Griffith | G01N 27/902 |
| | | | | 324/238 |
| 6,456,066 B1 | | 9/2002 | Burd et al. | |
| 2010/0017137 A1 | | 1/2010 | Legendre et al. | |
| 2010/0207620 A1 | | 8/2010 | Gies | |
| 2011/0068784 A1 | | 3/2011 | Sun et al. | |
| 2011/0127999 A1 | | 6/2011 | Lott et al. | |
| 2016/0168975 A1 | | 6/2016 | Donderici et al. | |
| 2016/0370166 A1 | | 12/2016 | Yang et al. | |

OTHER PUBLICATIONS

International Preliminary Report on Patentability received for counterpart International Application No. PCT/US2015/054735; dated Apr. 20, 2017; (12 pages).
International Search Report and Written Opinion received for counterpart International Application No. PCT/US2018/015908; dated Apr. 25, 2018, 17 pages.

* cited by examiner

MULTI-FREQUENCY EDDY CURRENT PIPELINE INSPECTION APPARATUS AND METHOD

CROSS-REFERENCE TO RELATED APPLICATION

This application claims the benefit of priority to U.S. Provisional Patent Application No. 62/062,599 filed Oct. 10, 2014, which is hereby incorporated by reference in its entirety.

TECHNICAL FIELD

The present technology is directed to methods and apparatus for inspecting a section of piping, in particular to non-invasive inspection methods.

BACKGROUND

Inspection of various piping systems and pipelines for defects, cracks, corrosion, wear and the like is important for maintaining the integrity of such systems, and avoiding potentially catastrophic consequences from failure of pipes during use. In some applications the piping systems are used to transport hot and/or corrosive materials. Often such piping systems are provided with an exterior layer of insulation or the like, which prevents visual inspection of the piping system, and inhibits conventional inspection systems that require direct access to the pipes. In another example, piping systems for transporting petroleum products or the like over large distances often include a thick layer of polymeric insulation and an outer metal sheathing. Such piping systems are extremely difficult and costly to effectively monitor for wear, corrosion, damage and similar defects. Other piping systems are difficult to access for other reasons. For example, piping systems and risers associated with off-shore drilling, including for example steel catenary risers, are substantially located underwater, and therefore difficult and expensive to monitor. Such piping systems may also be coated or encased with a protective outer casing, for example a plastic or elastomeric outer jacket.

Conventional state of the art pipe inspection systems typically use insertable inspection probes, called inline inspection pigs that are inserted directly into the pipe and travel along the pipe. An inspection pig may be self-propelled, or may be carried through the pipe by the flow within the pipe.

Different technologies are used in inspection pigs. For example, U.S. Pat. No. 7,218,102 to Nestleroth et al. discloses an inspection pig having three magnets that are in magnetic contact with the interior of the pipe wall, and relies on magnetic flux leakage detection from the pipeline wall to identify defects such as metal loss. In another example, U.S. Pat. No. 6,651,503 to Bazarov et al. discloses an inspection pig that uses ultrasonic flaw detection. One obvious disadvantage of inspection pigs is that they require access to the interior of a pipe. For many pipe systems, accessing the pipe to insert the inspection pig can be problematic, as it typically requires shutting down the flow within the pipe, and some disassembly and/or use of an access port.

It would be advantageous to provide a pipe inspection apparatus that may be used for inspecting the condition of the pipe even when the pipe is not easily accessible and/or is covered with a protective covering.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
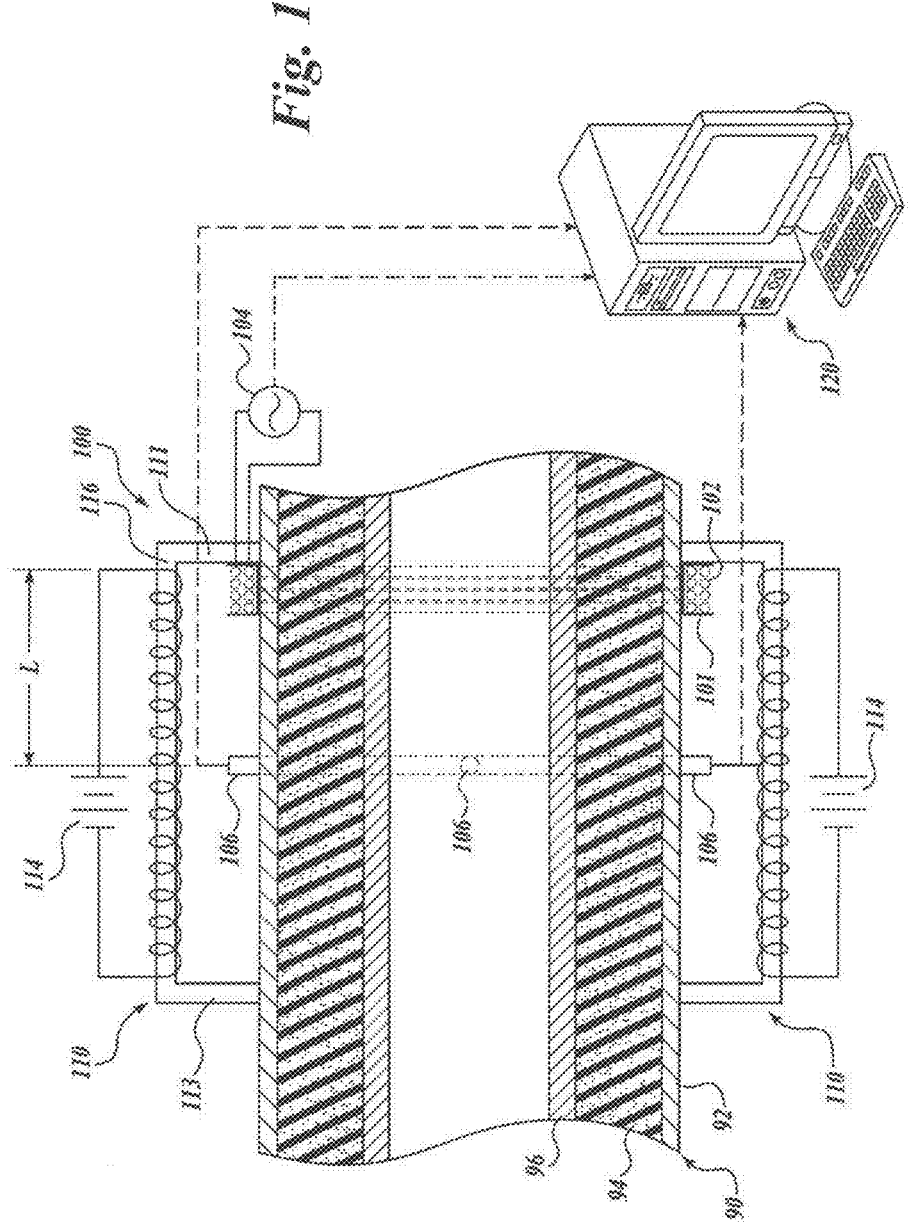
FIG. 1 is a diagram showing a pipe inspection apparatus in accordance with the present invention positioned for inspecting a section of insulated and sheathed pipe.
Figure 2:
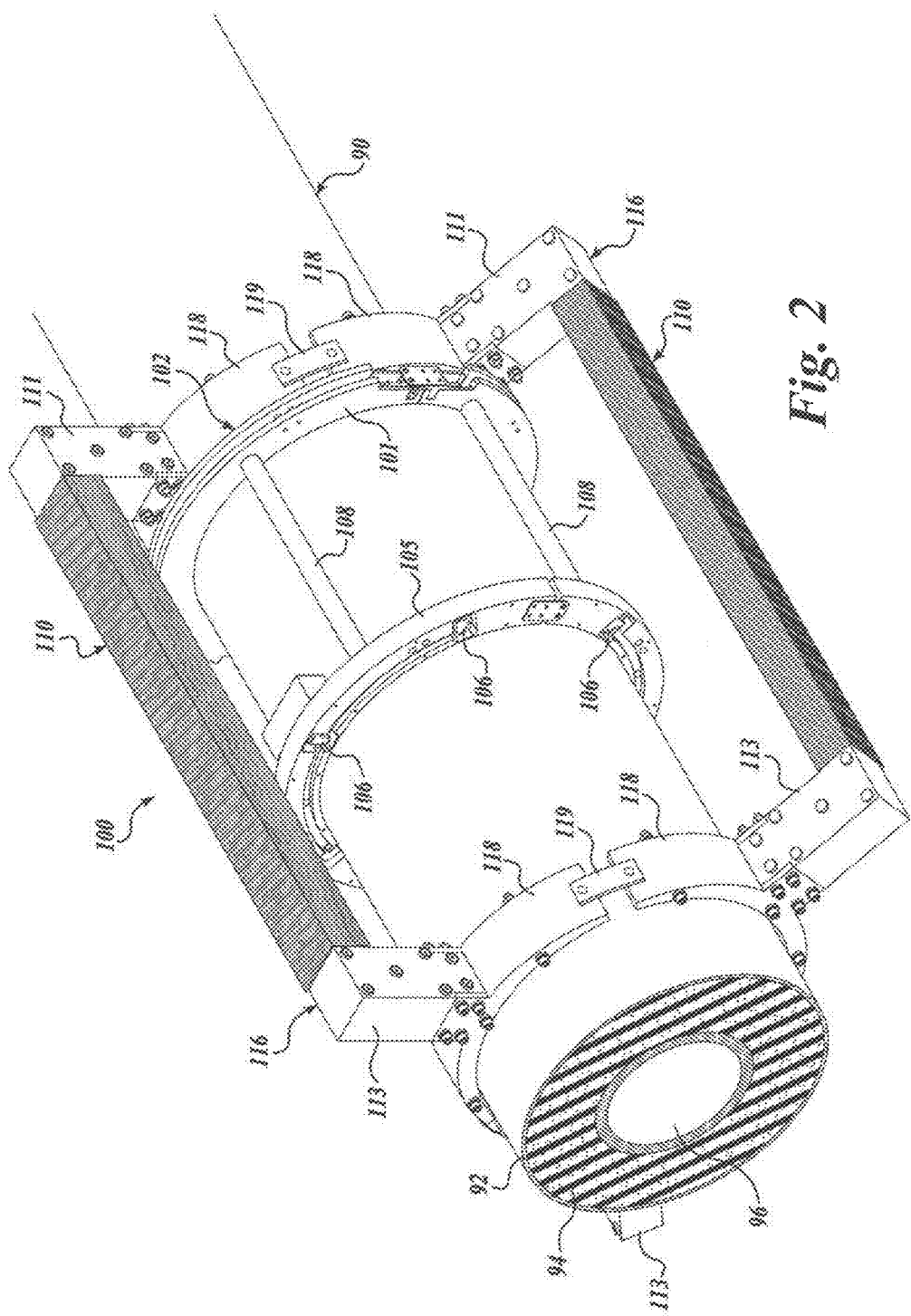
FIG. 2 is a perspective view of a first embodiment of the pipe inspection apparatus shown in FIG. 1, shown without the power supplies and data acquisition unit.
Figure 3:
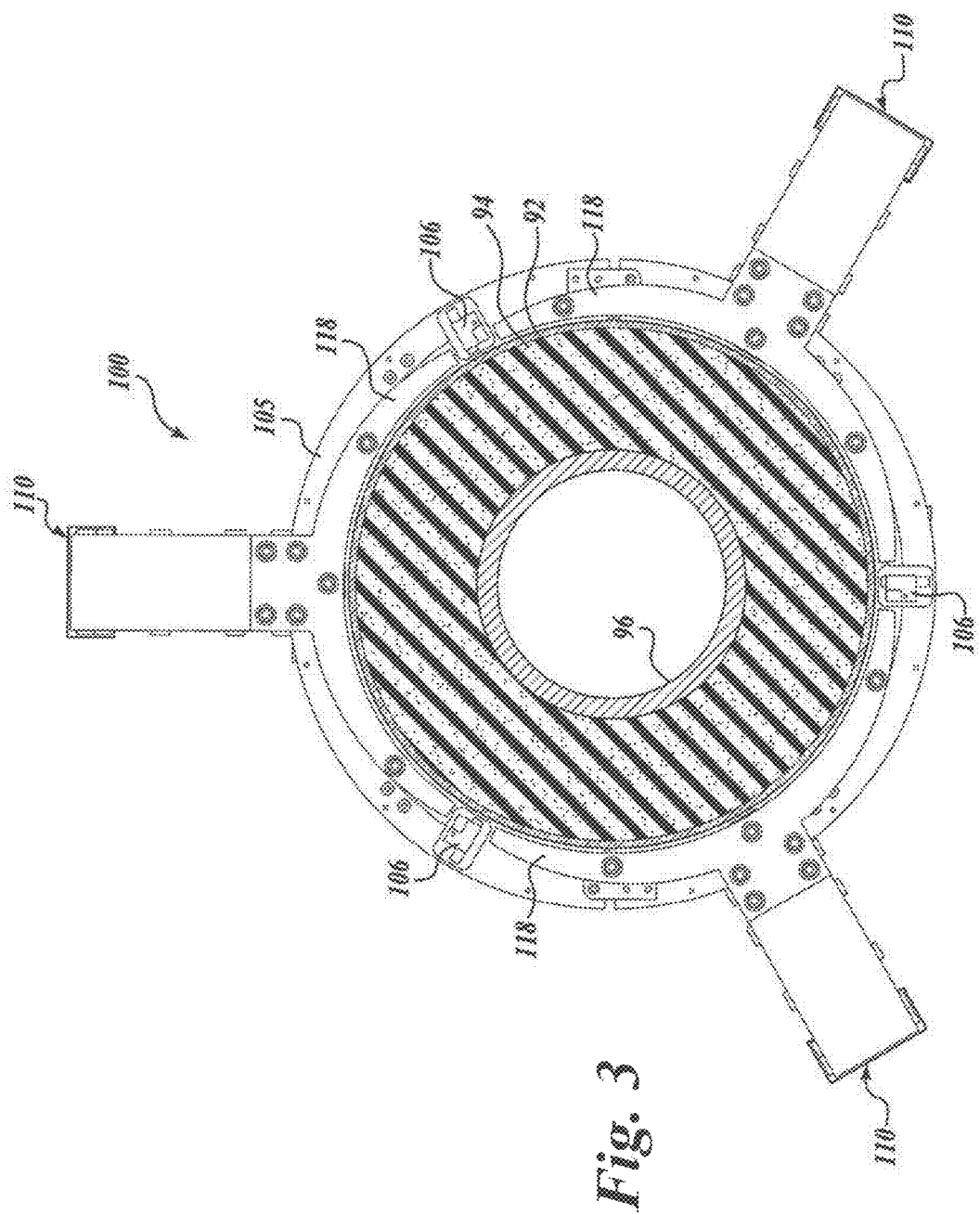
FIG. 3 is an end view of the pipe inspection apparatus shown in FIG. 2.

A first embodiment of an inspection system 100 in accordance with the present invention is shown schematically in FIG. 1. A perspective view of the pipe-mounted portions of the inspection system 100 is shown in FIG. 2, and an end view is shown in FIG. 3.

The inspection system 100 is particularly suitable for, but not limited to, inspecting a piping section 90 of the type having a magnetically permeable pipe 96 covered with a layer of insulation 94, and a magnetically permeable outer sheathing 92. In an exemplary above ground oil pipeline, for example, a steel pipe 96 approximately ½-inch in thickness is encased in an elastic polymeric insulation 94 that may be several inches thick. A galvanized steel sheathing 92 may be wrapped over the outer face of the insulation 94, and sealed to mitigate or prevent the intrusion of water into the pipeline. It will be appreciated by persons of skill in the art that a piping system such as this presents significant obstacles to nondestructive monitoring or inspecting of the condition of the pipe 96. For example, visual inspection is impossible without undertaking the arduous task of removing at least a portion of the sheathing 92 and insulation 94 from the pipe 96. The insulation 94 and the sheathing 92 also hinders placement of a probe in direct contact the pipe 96. The thickness of the insulation 94, in particular, prevents placing a probe in close proximity to the surface of the pipe 96. The sheathing 92 will typically interfere with conventional electromagnetic nondestructive examination (NDE) systems.

The inspection system 100 includes an excitation coil 102 that is positioned around the piping section 90 at a selected axial position. For convenience, the excitation coil 102 may be provided on a spool 101 having a hinge or other mechanism for opening the spool 101. For example, the coil 102 may be mounted on a hinged spool 101 wherein the individual loops of the coil 102 engage an electrical connector-type joint that is releasably engageable (not shown), such that the coil 102 may be opened for attachment to a piping section 90 from an intermediate location along the piping section 90.

An alternating current source 104 is operatively connected to the excitation coil 102, to selectively energize the coil 102. In this embodiment, the coil 102 is energized at a low frequency, for example less than 100 Hz, and for some applications less than 10 Hz. An excitation frequency of less than 5 Hz will be suitable for many pipeline applications. However, it will be appreciated that optimal frequency range will depend on the particular geometry of the piping to be examined. It is believed to be well within the skill in the art to identify a suitable frequency for a given piping section configuration.

A plurality of magnetic field detectors, for example magnetometers 106 are positioned about the piping section 90 at an axial distance L from the excitation coil 102. In a current embodiment the magnetometers 106 comprise vector magnetometers, and more particularly fluxgate magnetometers. A suitable power supply (not shown) for the magnetometers 106 is also provided. It is contemplated that other types of magnetic field detectors may alternatively be used, for example magnetoresistive magnetometers (e.g., giant magnetoresistive or anisotropic magnetoresistive magnetometers).

The magnetometers 106 are circumferentially spaced around the piping section 90 approximately adjacent the sheathing 92. For convenience the magnetometers 106 are mounted on an annular frame 105 for easy and consistent positioning. The frame 105 may also be hinged or otherwise openable, such that the magnetometers 106 may engage the piping section 90 from an intermediate location. In a current embodiment six fluxgate magnetometers 106 are positioned at equal circumferential intervals about the piping section 90. In another embodiment thirty-six (36) magnetometers are mounted to the frame. In general, it is believed that more magnetometers 106 will provide greater resolution of the condition of the pipe 96. More magnetometers 106 may be desired to examine, for example, larger diameter piping. As such magnetometers are preferably equally spaced around the pipe, multiples of magnetometers that evenly divide 360 degrees are typically utilized. As seen most clearly in FIG. 2, the spool 101 and magnetometer frame 105 may be interconnected with spacers 108, such as longitudinal rods or the like, to maintain a desired spacing between the coil 102 and the magnetometers 106.

A yoke assembly comprising a plurality of electromagnets 110 (three shown in FIG. 3) are mounted about the piping section 90, and positioned such that a first pole 111 of each of the electromagnets 110 is disposed adjacent the coil 102, and the opposite pole 113 is positioned on the other side of the magnetometers 106 such that the magnetometers 106 are positioned approximately at the midpoint between the poles 111, 113 of the electromagnets 110. The ferromagnetic core 116 of each of the electromagnets 110 is formed with leg portions that extend from either end of the core 116 and engage curved supports 118 that are shaped to abut the outer sheathing 92 of the piping section 90. Releasable connectors 119 interconnect the curved supports 118, and hold them securely to the piping section 90.

Referring again to FIG. 1, one or more DC power supplies 114 provide power to energize the electromagnets 110. It will now be appreciated that the electromagnets 110 produce a magnetic field that at least partially saturates the magnetically permeable outer sheathing 92, thereby improving the ability of the excitation coil 102 to induce eddy currents in the pipe 96. The magnetometers 106 are preferably located midway between the poles 111, 113 to minimize or eliminate interference from the magnetic field produced by the electromagnets 110, optimizing the ability of the magnetometers 106 to detect the magnetic fields induced by the eddy currents in the pipe 96. Although electromagnets 110 are shown and currently preferred, it is contemplated that other magnetic means, for example rare earth magnets or the like, may alternatively be used. Alternatively, as indicated by the second embodiment below, the inspection may be conducted without the electromagnets 110. For example, in piping configurations wherein no magnetically permeable sheathing 92 is present, the system without electromagnets may be preferred. Even in applications wherein a sheathing 92 is present the electromagnets 110 may not be used so long as magnetic fields generated from eddy currents induced in the pipe 96 by the coil 102 can be adequately detected. Generally, embodiments of the technology may be used for inspecting pipes of different configurations, for example, pipes not having insulation disposed between a sheathing and the pipe, or not having a sheathing covering the pipe. Embodiments of the technology may be used for inspecting pipes having different sheathing materials. For example, pipes having non-metallic sheathing or coating, such as those having concrete coatings or having high-density polyethylene coatings, may be inspected using embodiments of the technology.

A data acquisition system 120 is operatively connected to the magnetometers 106 and the AC power supply 104. The data acquisition system 120 controls or monitors the application of the AC power to the excitation coil 102, and receives the sensor date from the magnetometers 106, which data is used to evaluate and inspect the pipe 96 in the vicinity of the magnetometers 106. The data acquisition system 120 may be physically connected to the system 100 or wireless means may be used to communicate with the other components of the system, as is well-known in the industry.

It should also be appreciated that although a separate data acquisition system 120 and AC power supply 104 are indicated in FIG. 1, it is contemplated and will be within the skill in the art to alternatively provide an on-board microcomputer board or the like and a suitable power supply to control the operation and record data received from the magnetometers 106, providing a stand-alone pipe-mounted systems.

It is also contemplated that automated operation of the system may be readily accomplished by providing components for sensing the position and/or movement of the system 100. For example, in a current embodiment the system is provided with a global positioning system (GPS) module, and with triaxial accelerometers. Data from the GPS, accelerometers and magnetometers may be wirelessly transmitted to an on-board or remote data acquisition system.

To inspect a piping section 90 the excitation coil 102 and magnetometers 106 are placed about the piping section 90. The yoke assembly electromagnets 110 are positioned such that the first poles 111 are disposed approximately adjacent the excitation coil 102, with the magnetometers 106 located approximately midway between the first poles 111 and opposite poles 113. The electromagnets 110 are powered to produce the desired magnetic field, and a low frequency current is applied to the excitation coil 102. The responsive signals from the magnetometers 106 are received by the data acquisition unit 120. The entire assembly is then moved axially along the piping section 90, and the magnetometer 106 data sequentially recorded. The data is then analyzed to identify and evaluate locations of defects in the pipe 96.

It will be appreciated by persons of skill in the art that the eddy currents produced in the pipe 96 by the excitation coil 102 will be impacted by defects or other anomalies in the pipe such as cracks, corrosion, pitting or the like. Changes in the eddy currents produced in the pipe 96 will cause corresponding changes in the magnetic fields induced by the eddy currents. Therefore, the data received from the magnetometers 106 may be used to identify defects and/or regions of concern in the pipe 96. It is contemplated that the process of moving the pipe inspection system 100 axially along the piping section 90 may be automated.

In some embodiments, the magnetometers 106 are configured to detect magnetic flux along the axial direction. In some embodiments, the magnetometers 106 can be configured to instead detect magnetic flux along the radial direction. In certain embodiments, two rings of magnetometers may be provided, with some magnetometers detecting magnetic flux in the axial direction, and other magnetometers detecting magnetic flux in the radial direction. The different measurements of magnetic flux may be carried out sequentially (e.g., first the axial magnetic flux is measured, followed by measurement of the radial magnetic flux), or in some embodiments the measurements may be carried out simultaneously.

Figure 4:
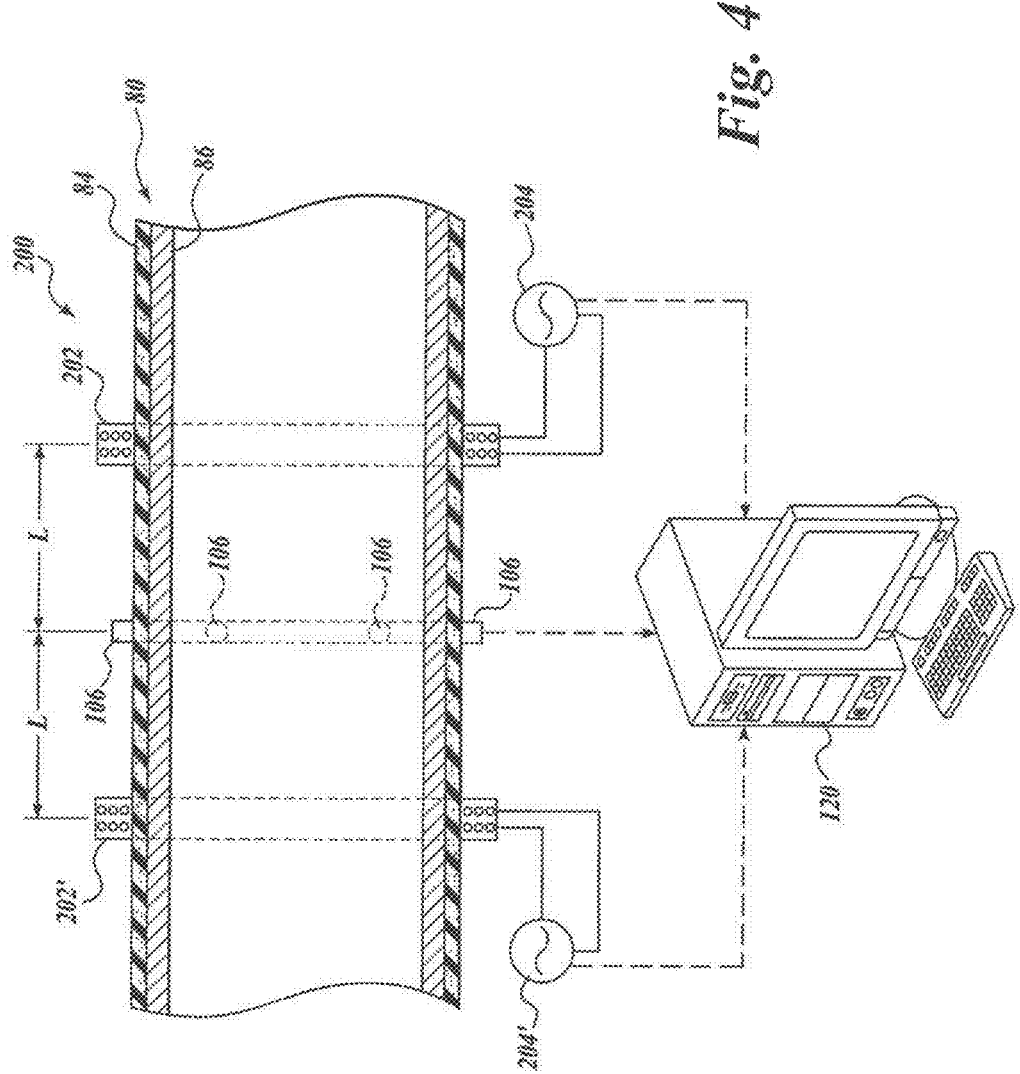
FIG. 4 is a diagram showing a second embodiment of a pipe inspection apparatus in accordance with the present invention, positioned for inspecting a section of sheathed piping.

A second embodiment of a pipe inspection system 200 in accordance with the present technology is shown schematically in FIG. 4, disposed on a piping section 80 comprising a pipe 86 that is encased or covered with a sheath or protective covering 84, which may be formed for example from a polymeric material. The piping section 80 may be, for example, an undersea pipe or pipe riser, for example a steel catenary riser or the like. In this embodiment the inspection system 200 includes two spaced-apart excitation coils 202, 202'. The excitation coils 202, 202' may be substantially similar to the excitation coil 102 described above, and may be mounted on spools 101 or the like. The magnetometers 106 are circumferentially spaced around the piping section 86, and are located midway between the excitation coils 202 and 202', such that the magnetometers 106 are a distance L from each excitation coil 202, 202'.

The first excitation coil 202 is connected to an AC power supply 204 that produces a first alternating current, and the second excitation coil 202' is connected to the AC power supply 204' such that the second excitation coil is energized with a second alternating current that is of opposite polarity but otherwise the same as the first alternating current. The AC power supply 204' may be a separate power supply from AC power supply 204, but preferably is the same power supply, simply wired series opposing such that an opposite polarity signal is applied to the second excitation coil 202'. In some embodiments, the excitation coils 202, 202' can be energized with similar alternating currents having the same polarity.

Excitation currents ranging from 2 amps to 20 amps have been used and found to be effective, with the eddy current signal strength increasing with increasing excitation current. Use of excitation currents greater than 20 amps is also contemplated. In an exemplary embodiment an excitation current pulse is applied for approximately 1.5 seconds at each testing point, so the total power requirements even at higher amperages are not prohibitive.

Figure 5:
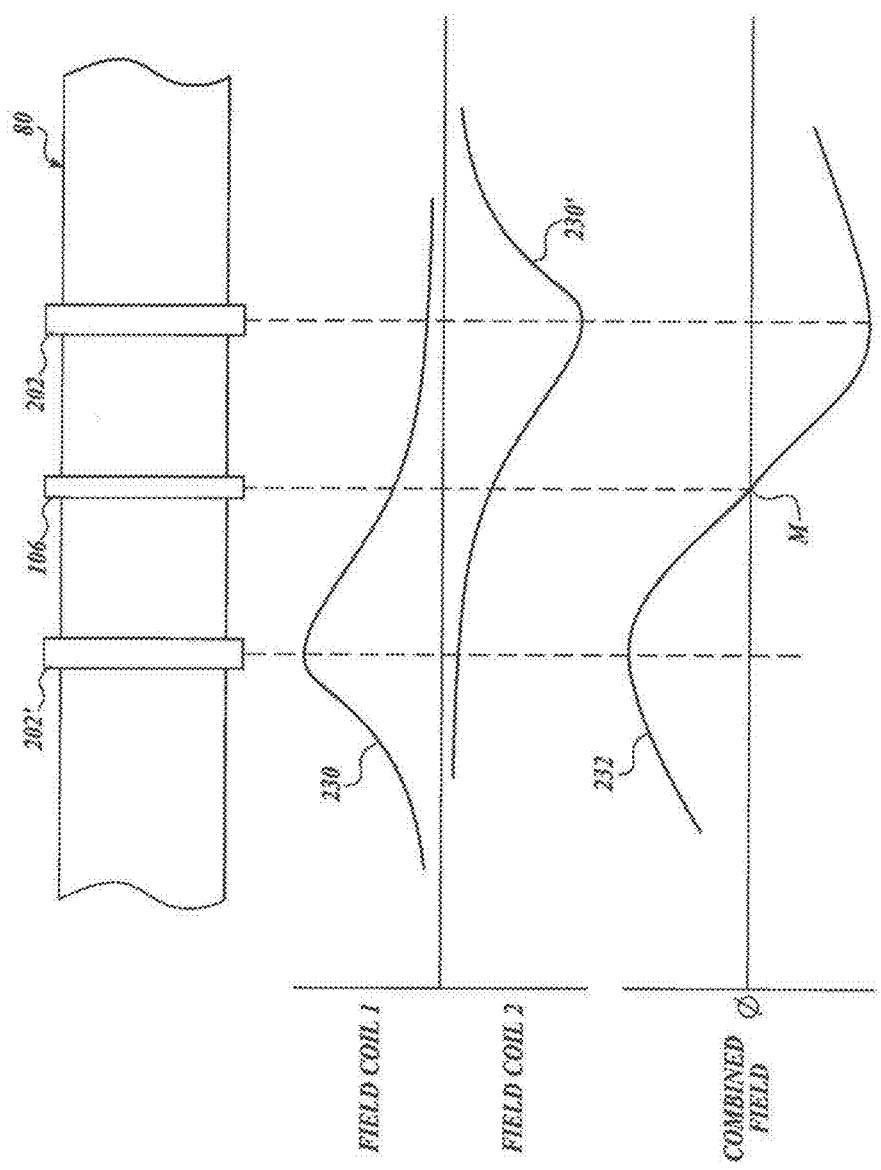
FIG. 5 shows qualitatively the magnetic field induced by the first and second excitation coils of the apparatus shown in FIG. 4, as a function of axial distance along the section of piping.

FIG. 5 shows schematically and qualitatively the magnetic field 230 induced by the first excitation coil 202, and the magnetic field 230' induced by the second excitation coil 202' as a function of axial distance along the piping section 80, when the coils are driven by equal but reverse polarity currents. FIG. 5 also shows the combined magnetic field 232. It will be appreciated that although the combined magnetic field varies over the piping section 80, the combined field is approximately zero at the location M of the magnetometers 106. It will be appreciated by persons of skill in the art, based on the disclosure herein, that the zeroing of the magnetic field at the location M of the magnetometers 106 improves the sensitivity of the magnetometers 106 to the magnetic fields induced by eddy currents in the pipe 86.

Although the second embodiment inspection system 200 is illustrated on a piping section without a magnetically permeable outer sheathing, the system 200 has also been used on piping sections 90 such as that shown in FIG. 1, and produces good results. The second embodiment 200 is also believed to be suitable for applications where access may be difficult, such as subsea piping and riser systems because no yoke assembly is required.

It will be appreciated that the coils 202, 202', magnetometers 106 and associated components may be conveniently housed, for example in a clamshell-style composite housing (not shown). The assembly is moved along the piping section 80, and the coils 202, 202' are periodically energized. The eddy current signal recorded by the magnetometers 106 are recorded to a data acquisition unit. As discussed above, optional motion tracking systems, such as accelerometers and/or GPS systems may be provided to detect and track the motion of the system 200 along the piping section 80. It is contemplated that the system 200 may be provided with a drive system (not shown) for automatically moving the system 200 along the piping section 80, or may be configured for manual operation.

Figure 6:
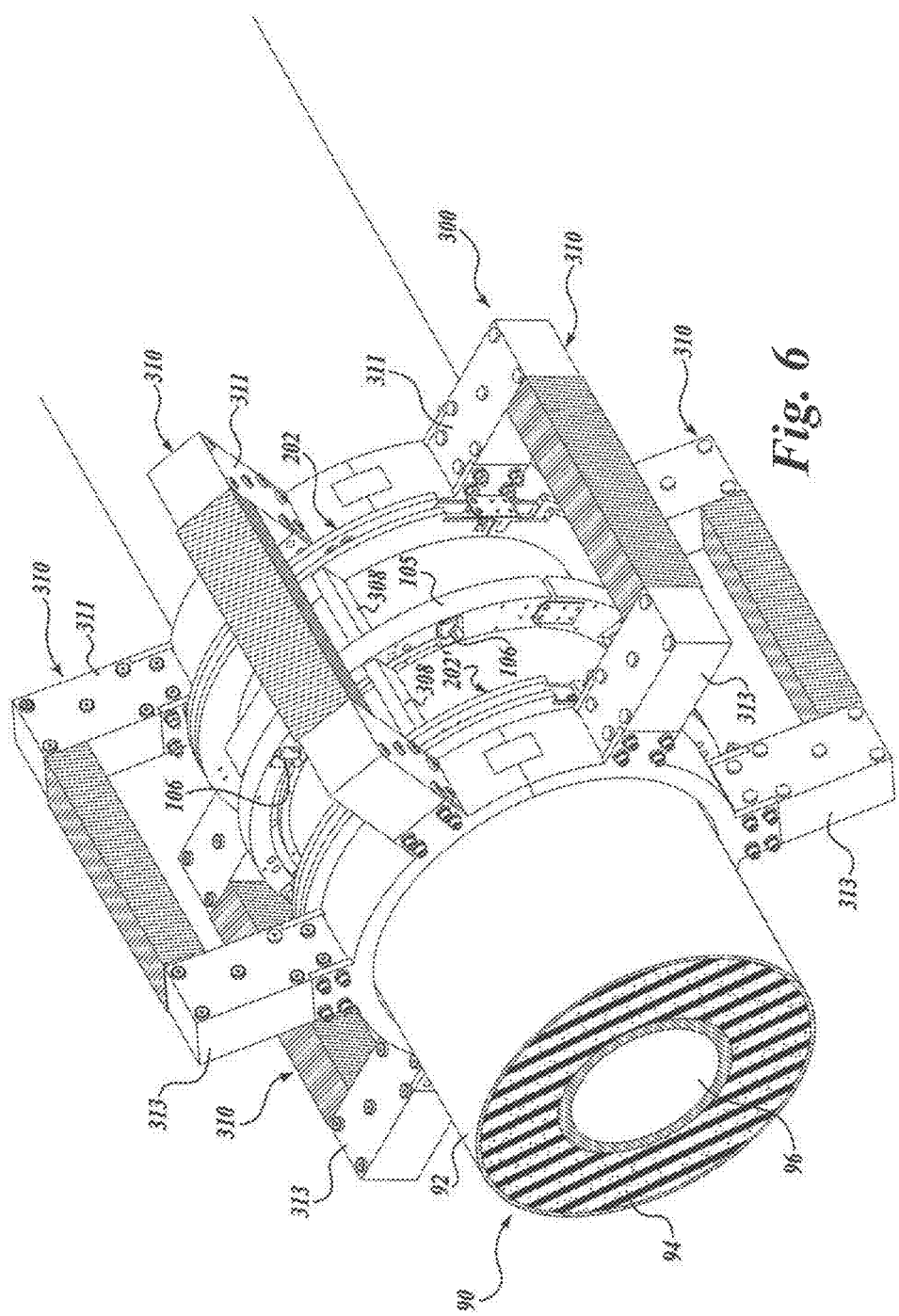
FIG. 6 is a perspective view of a third embodiment of a pipe inspection apparatus in accordance with the present invention, shown on a section of insulated and sheathed pipe, and without the power supplies and data acquisition unit.
Figure 7:
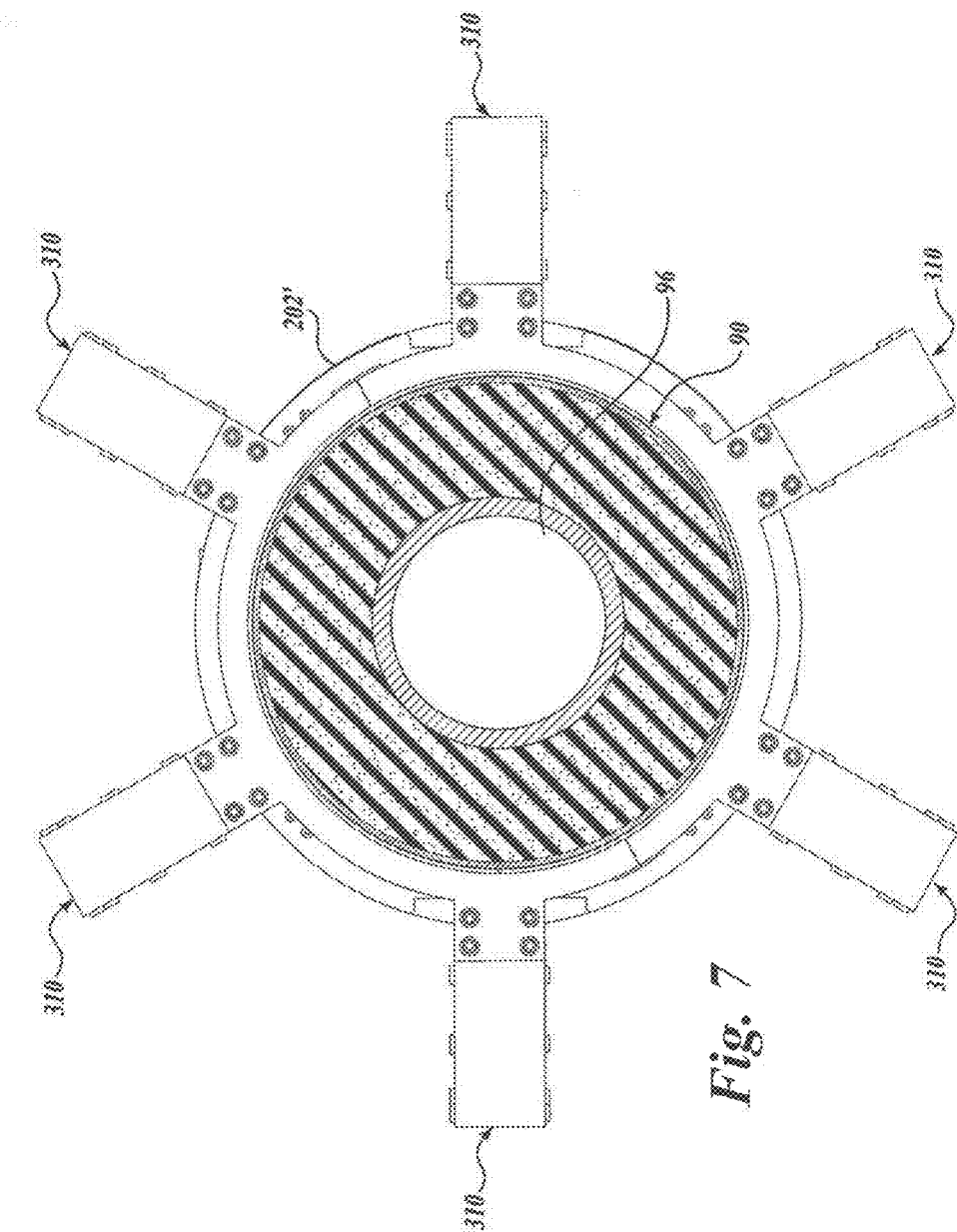
FIG. 7 is an end view of the pipe inspection apparatus shown in FIG. 6.

A third embodiment of a pipe inspection system 300 in accordance with the present technology is disclosed in FIGS. 6 and 7 (without the power supplies, or data acquisition unit). This embodiment generally combines the first and second embodiments disclosed above. The third system 300 uses two excitation coils 202, 202' similar to the second embodiment 200 described above. The excitation coils 202, 202' can be energized with similar, but opposite polarity alternating currents, as discussed above. In some embodiments, the excitation coils 202, 202' can be energized with similar alternating currents having the same polarity.

A yoke assembly similar to the first embodiment 100 described above is also provided. In this embodiment, the yoke assembly comprises six electromagnets 310, equally spaced about the piping section 90. The first excitation coil 202 is disposed adjacent a first pole 311 of the electromagnets 310, and the second excitation coil 202' is disposed adjacent the opposite pole 313. It will be appreciated that the use of electromagnets 310 (in this case six rather than three) permits a strong saturating magnetic field to be induced in the sheathing 92 with a shorter overall system length. Although electromagnets are disclosed, it is contemplated that other magnetic means, such as permanent magnets, may alternatively be used.

The magnetometers 106 are located midway between the two excitation coils 202, 202' and therefore also midway between the first pole 311 and opposite pole 313 of the electromagnets 310. The magnetometers 106 are therefore at a centered position with respect to the magnetic field induced by the electromagnets 310, and at a centered position with respect to the two excitation coils 202, 202'.

Figure 8A:
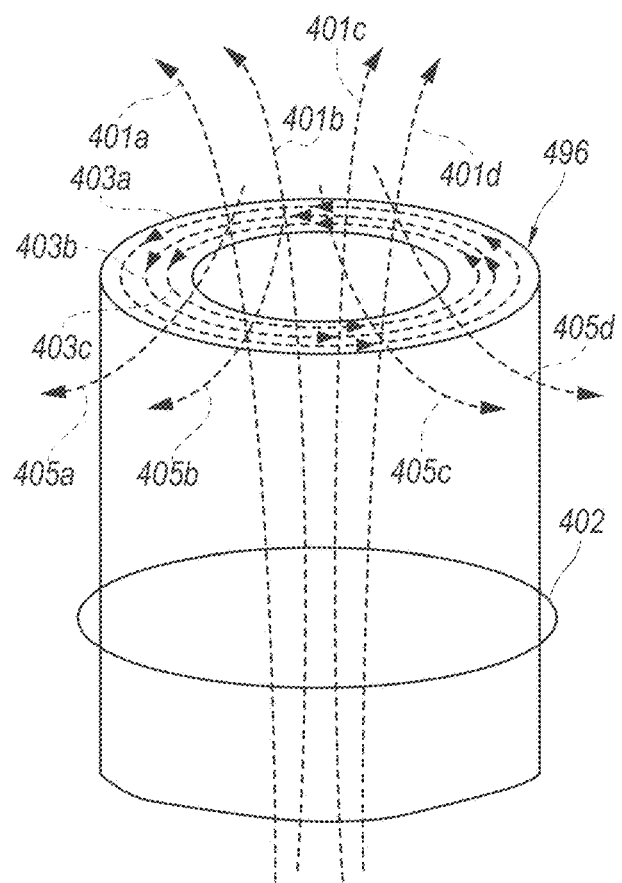
FIGS. 8A-8B are schematic side perspective and top views, respectively, of an excitation coil disposed adjacent to a section of pipe.
Figure 8B:
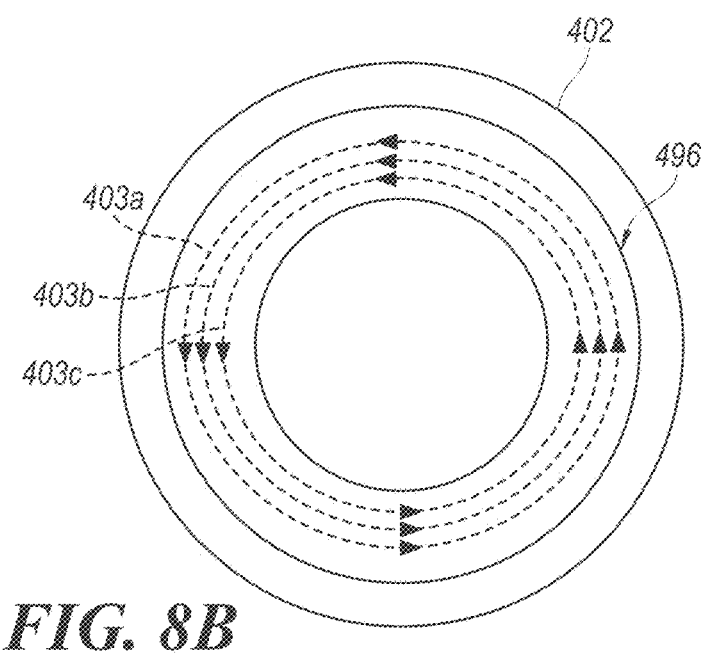

FIGS. 8A-8B are schematic side perspective and top views, respectively, of an excitation coil disposed adjacent a section of pipe. As illustrated, excitation coil 402 surrounds a segment of pipe 496. The excitation coil 402 can be substantially similar to the excitation coils 102, 202, and 202' described above. Running alternating current through the excitation coil 402 induces a changing primary magnetic field disposed generally axially along the pipe 496, as indicated by field lines 401a-d. This primary magnetic field in turn induces the eddy currents 403a-c at varying depths within the pipe 496. Eddy currents 403a-c then induce the secondary magnetic fields indicated by field lines 405a-d. As noted previously, eddy currents 403a-c produced in the pipe 496 by the excitation coil 402 will be impacted by defects or other anomalies in the pipe 496 such as cracks, corrosion, pitting or the like. Changes in the eddy currents 403a-c will in turn cause corresponding changes in the secondary magnetic fields 405a-d induced by the eddy currents 403a-c.

A second excitation coil (not shown) can be positioned around the pipe 496 at an axial distance from the first excitation coil 402. A second input AC signal can be supplied to the second excitation coil. In some embodiments, the second input is identical to the first input but with opposite polarity. In some embodiments, the excitation coils can be energized with alternating currents having the same polarity. In some embodiments, the alternating currents may be partially shifted with respect to each other such that they do not have the same or opposite polarities.

A plurality of magnetometers (not shown) are positioned radially around the pipe 496 to detect the secondary magnetic fields 405a-d. As noted above, the secondary magnetic fields 405a-d will be affected by defects or other anomalies in the pipe 496, due to their effects on the eddy currents 403a-c. The input signals can be captured in the time domain and a Fast Fourier Transform (FFT) can be used to retrieve the amplitude and phase information for the input signals. The detected secondary magnetic fields observed by each magnetometer are likewise captured in the time domain and a FFT can be used to retrieve amplitude and phase information for the output signals of each magnetometer. These two sets of complex quantities can be divided, providing normalized responses for each magnetometer. The derived normalized responses can then be used to detect any defects within the pipeline.

As illustrated, eddy currents 403a-c are produced at different depths within the pipe 496. Depending on the frequency of the AC applied to the excitation coil 402, various depths can be achieved. For example, a higher frequency current applied to the excitation coil 402 may induce a relatively shallow eddy current 403a (i.e., closer to the outer surface of the pipe 496). A lower frequency current applied to the excitation coil 402 may in turn induce a relatively deeper eddy current 403c (i.e., closer to the inner surface of the pipe 496). The depth of the eddy current will depend on the characteristics of the AC signal applied to the excitation coil, the configuration of the coil, and the dimensions and materials of the pipe itself. In cases involving metallic pipes, a relatively low (e.g., <500 Hz) frequency may be sufficient to induce the desired eddy currents. In cases involving composite pipes (rather than metallic), a significantly higher frequency (e.g., 20 GHz) may be applied to induce currents.

Figure 9:
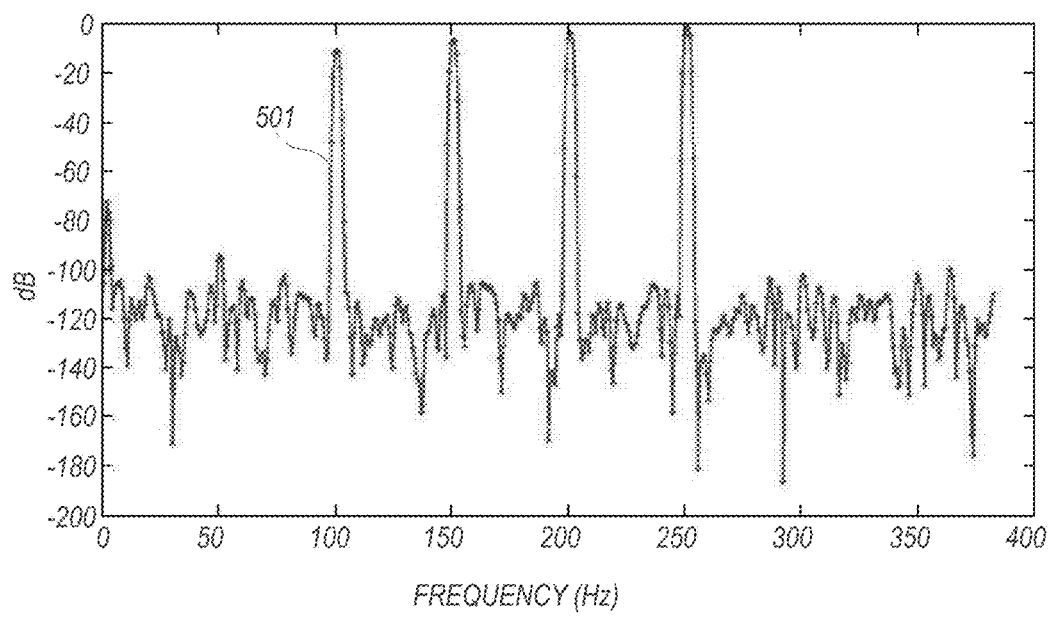
FIG. 9 is a frequency-domain graph of a magnetometer output signal.

By utilizing varying frequencies to produce eddy currents of varying depths, the depth of a defect can be detected in addition to detecting its axial location. For example, a scan including multiple frequencies applied sequentially can indicate both the axial location of the defect as well as the depth of the defect. The use of multiple frequencies applied sequentially, however, can be time-consuming. To expedite the process, a synthesized multi-frequency waveform can be applied to the excitation coil 402. FIG. 9 illustrates a resultant output detected at a magnetometer when a multi-frequency waveform is supplied to the excitation coil 402. The illustrated output signal 501 is displayed in the frequency domain. As illustrated, the peaks at 100 Hz, 150 Hz, 200 Hz, and 250 Hz indicate that these four frequencies are being applied, and the resulting eddy currents measured, simultaneously via the multi-frequency waveform. These four frequencies are each sensitive to defects at different depths of the pipe. By utilizing this synthesized multi-waveform input signal, a range of depths can therefore be measured simultaneously. A multi-waveform approach therefore increases the speed of analysis, and can also decrease the signal-to-noise ratio for any identified defects as will be described in additional detail below.

In various embodiments the waveform can be synthesized using a field programmable gate array (FPGA). At the highest level, FPGAs are reprogrammable silicon chips. Using prebuilt logic blocks and programmable routing resources, these chips can be configured to implement custom hardware functionality. Accordingly, FPGAs provide the same flexibility of software running on a processor-based system, but are not limited by the number of processing cores available. Unlike processors, FPGAs are truly parallel in nature, so different processing operations do not have to compete for the same resources. Each independent processing task is assigned to a dedicated section of the chip, and can function autonomously without any influence from other logic blocks. As a result, the performance of one part of the application is not affected when more processing is added.

Although the illustrated embodiments utilize four frequencies, more or fewer may be used. For example, in some embodiments, the multi-frequency waveform can incorporate two frequencies, or in other embodiments the multi-frequency waveform can incorporate three, four, five, six frequencies or more. In some embodiments, the multi-frequency waveform can incorporate up to 16 frequencies, and other embodiments may incorporate even more. As noted above, one advantage of utilizing a greater number of frequencies is that this approach allows use of low-frequency signals (e.g., 5 Hz) to detect very deep defects while at the same time using higher frequencies signals (e.g., 250 Hz) to detect shallower defects. Another advantage of utilizing AC input signals is that continuous motion of the inspection apparatus along the pipeline can be maintained. In contrast, using transient current input signals requires incremental movement steps punctuated by periods of rest. In some embodiments, the apparatus is sufficiently sensitive to detect defects in the pipeline with a minimum size of 3T×3T×0.2T, where T is the nominal thickness of the pipe. In some embodiments, the apparatus is sufficiently sensitive to detect defects with a minimum size of 1T×1T×0.1T.

Data representing the detected magnetic fields can be presented in a number of visual forms, for example in some embodiments a color-shading graph can be provided with varying colors reflecting the magnitude of the detected secondary magnetic fields induced by the eddy currents. Such a color-shaded graph can provide a simple and effective way to rapidly identify any defects in the pipe due to anomalous or irregular shading patterns. In some embodiments, the system can automatically analyze data from the detected magnetic fields to determine whether a defect has been identified without the need for an operator to visually inspect a graphical output. For example, a threshold filter or other such filter can determine whether the detected secondary magnetic fields in a given region of the pipeline deviate from the mean values by more than a predetermined amount. If this condition is satisfied, the defect is flagged at that location. In some embodiments, such a filter can be configured to detect defects when deviations are detected over a certain pre-determined size threshold, so as to avoid false positives associated with small deviations in isolated areas that do not correspond to actual defects in the pipeline. In some embodiments, such an automatically detected defect can trigger an alarm or other such indicator that a defect has been found in the pipeline.

As noted above, during inspection the assembly is moved along the piping section. The eddy current signals measured by the magnetometers are recorded to a data acquisition unit. An optional motion tracking system, such as accelerometers and/or GPS systems may be provided to detect and track the motion of the system along the piping section. It is contemplated that the system may be provided with a drive system (not shown) for automatically moving the system along the piping section, or may be configured for manual operation. In some embodiments, the drive system can move the assembly along the pipeline continuously at a rate of at least 5 feet per minute. In some embodiments, the drive system can move the assembly along the pipeline in steps, for example 1-inch increments, at a rate of at least 5 feet per minute.

Embodiments of the pipeline inspection assembly can be adapted for pipes of various sizes, for example ranging from 4 inches to 24 inches outer diameter. Some embodiments may be adapted for inspecting pipes having layers of insulation around the pipe, for example up to 4 inches thick. In such embodiments, physical dimensions of the spool 101 can be configured to accommodate the larger pipeline. The size of the excitation coils 102, 202, 402 can likewise be configured to accommodate a particular size pipeline, for example by being formed with greater or smaller radii, and/or by increasing the length of the coils. In embodiments of the pipeline inspection assembly that are configured for use with larger pipelines, the number of magnetometers 106 can be increased to maintain sufficient resolution in detecting defects in the pipeline.

Figure 10:
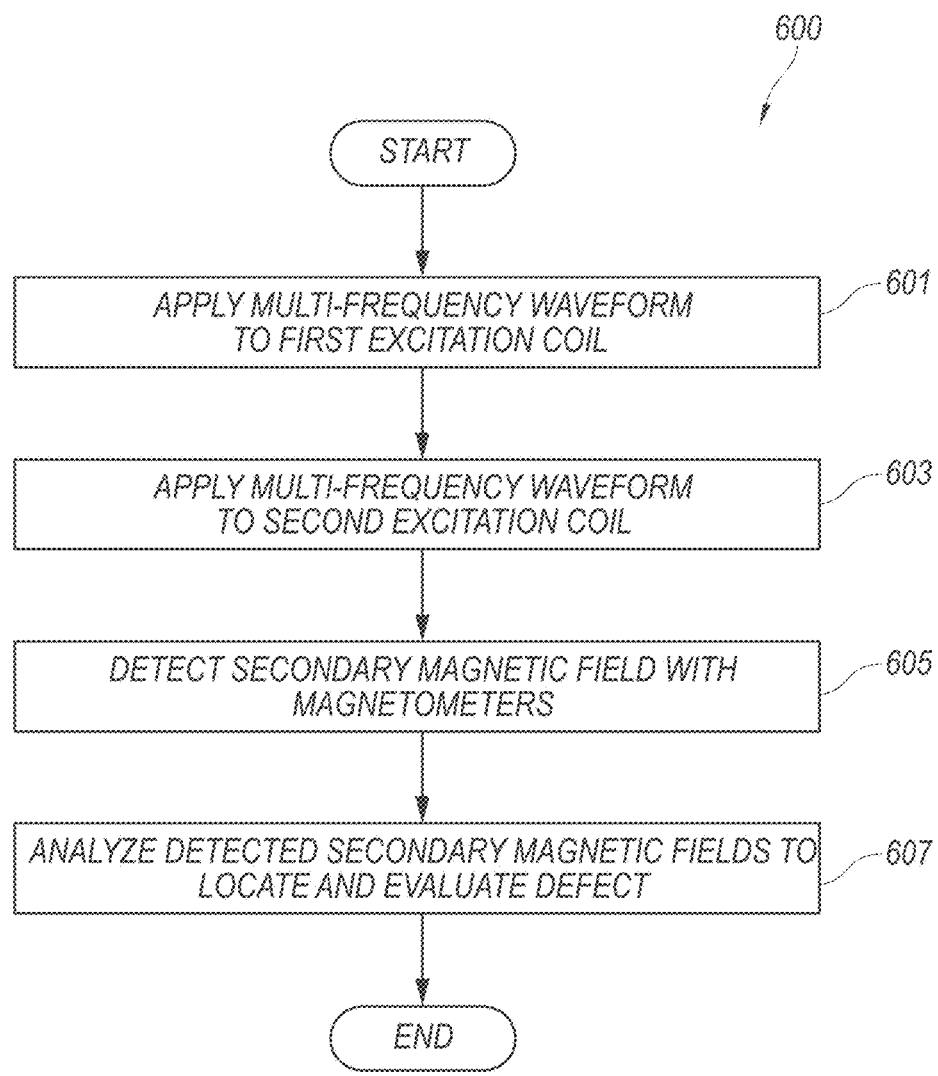
FIG. 10 is a flow diagram of a method for analyzing a section of pipeline with a multi-frequency waveform.

FIG. 10 is a flow diagram of a method for analyzing section of pipeline with a multi-frequency waveform. The process 600 begins in block 601 by applying a multi-frequency waveform to a first excitation coil. As described above, the multi-frequency waveform can be synthesized from a number of frequencies, for example 2, 4, 6, 8, 10, 16, or more. The first excitation coil can be positioned around a section of pipe and located so as to induce eddy currents in the pipe. Process 600 continues in block 603 with applying the multi-frequency waveform to a second excitation coil. In some embodiments, the multi-frequency waveform applied to the first excitation coil can have the same polarity as the multi-frequency waveform applied to the second excitation coil, and the two multi-frequency waveforms can be in phase with one another. In this configuration, the multi-frequency waveforms constructively interfere along the axial direction, while the induced secondary magnetic fields (extending generally along the radial direction) will destructively interfere, thereby increasing sensitivity in measuring disturbances of these secondary magnetic fields. In other embodiments, the multi-frequency waveform applied to the first excitation coil can have a first polarity and the multi-frequency waveform applied to the second excitation coil can have a second, opposite polarity.

The second excitation coil can be similarly disposed around a section of pipeline, and can be positioned at an axial distance from the first excitation coil. Process 600 continues in block 605 with detecting secondary magnetic fields with magnetometers. As described above, a plurality of magnetometers can be radially spaced around a section of piping, for example at an axial position substantially centrally between the first and second excitation coils. Process 600 continues in block 607 with analyzing the detected secondary magnetic fields to locate and evaluate a defect. As noted previously, the output signals detected by the magnetic fields can be indicative of a defect in the pipe due to effects on the eddy currents in the pipe. In some embodiments, the output signal is used to determine both the axial location of a defect, as well as the radial location (i.e., the depth within the pipe). As noted above, the higher frequency components of the multi-frequency waveform may be more sensitive to defects in shallower portions of the pipe, while the lower frequency components of the multi-frequency waveform can be more sensitive to defects in the deeper portions of the pipe. As a result, aberrations detected in the output signal can be analyzed to determine the depth of any detected defect.

In various embodiments described above, the excitation coils are energized with continuous AC power. An alternative approach to detecting and evaluating defects in the pipeline involves the application of transient current through the excitation coils. For example, a brief pulse on the order of 10 amps can be supplied to the excitation coils. In some embodiments, the pulse can be on the order of 50 ms. In some embodiments, a brief pulse of transient current can be supplied to either or both of the excitation coils, at the same time or in sequence. When the power to the excitation coils is turned off, the current in the excitation coils decays exponentially to zero within a period on the order of a few milliseconds. The changing current in the excitation coils induces a changing magnetic flux, in turn inducing transient eddy currents in the pipe, which then produce secondary magnetic fields measured by the magnetometers. The secondary magnetic fields decay rapidly. By analyzing the decay profile and magnitude of detected secondary magnetic fields, the axial location and depth of defects can be identified, including subsurface flaws. For example, a subsurface defect excited by a current pulse in a coil gives rise to a secondary magnetic field that reaches a peak at some time after the current change in the drive coil. The delay time between the drive coil current transition and the detected change in the secondary magnetic field depends in part on the depth of the defect below the surface of the pipe. Discrimination in depth and the ability to estimate wall thickness though variations in the relaxation time of induced current as detected by magnetic field sensors means that corrosion loss in pipes can be identified, located and quantified.

The magnetometers can obtain magnetic flux measurements as a function of time and position. The variation of the secondary magnetic field in space due to local material loss is equivalent to that of a magnetic dipole distribution at the flaw. In other words, the magnetic dipole distribution can be used to model the variation due to local material loss. The characteristics of the dipole field provide one means of interpreting signals generated as a result of material loss.

The temporal variation is characterized by the rate at which the secondary magnetic field decreases after the excitation coil current is reduced to zero. The relaxation of the field can be approximated by an exponential decay over a limited interval. Where the wall thickness has been diminished by corrosion or other defect, the characteristic relaxation time of the signal will be reduced for both internal and external corrosion loss. If the corrosion (material loss) is external, the loss is evident from the dipole character of the spatial domain response at an early stage. If the corrosion (material loss) is internal, the dipole effect on the field amplitude occurs later due to the time taken for the field to diffuse through the reduced pipe wall.

Figure 11:
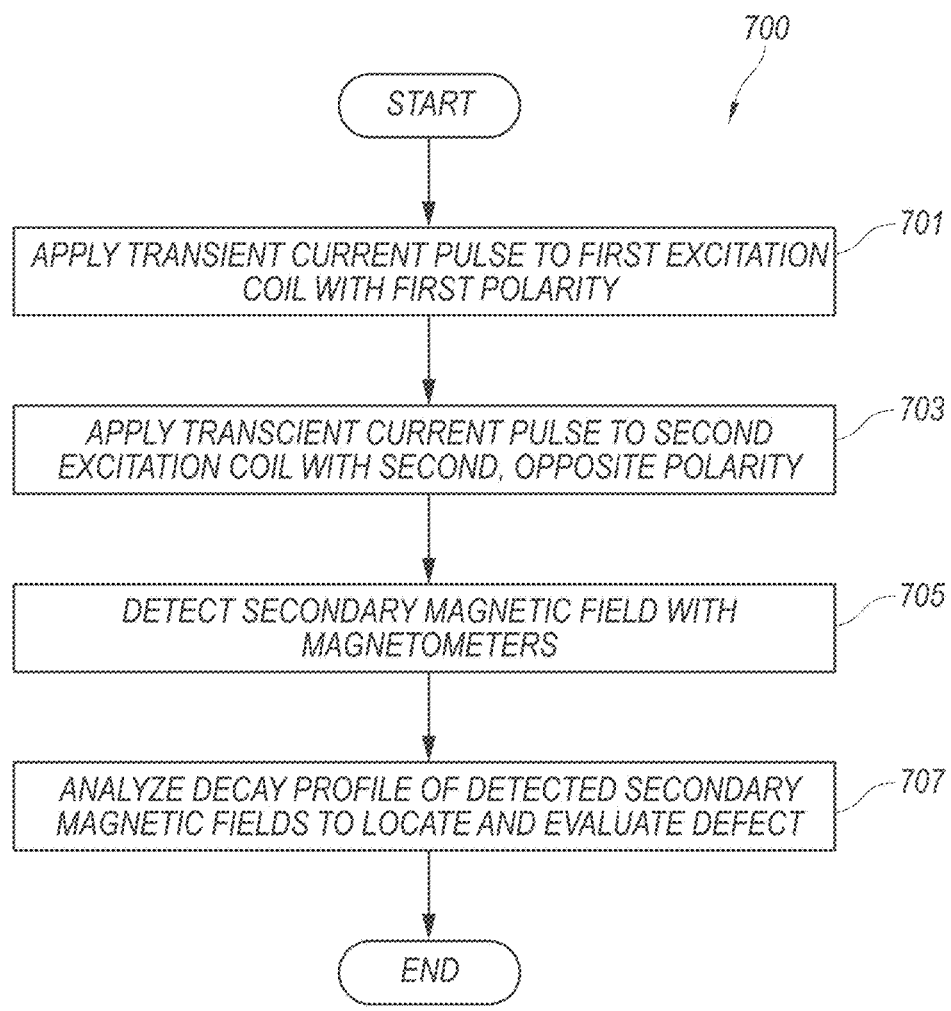
FIG. 11 is a flow diagram of a method for analyzing a section of pipeline with a pulsed transient eddy current technique.

FIG. 11 is a flow diagram of a method for analyzing a section of pipeline with a pulsed eddy current technique. The process 700 begins in block 701 with applying a pulse of transient current to a first excitation coil with a first polarity. The first excitation coil can be positioned around a section of pipe and disposed so as to induce eddy currents in the pipe. Process 700 continues in block 703 with applying a similar pulse of transient current to a second excitation coil with a second, opposite polarity. The second excitation coil can be similarly disposed around a section of pipeline, and can be positioned at an axial distance from the first excitation coil. The first and second transient pulses may be applied simultaneously. In some embodiments, the first and second transient current pulses may be separated in time, for example by between 20 µs and 750 µs. Process 700 continues in block 705 with detecting secondary magnetic fields with magnetometers. As described above, a plurality of magnetometers can be radially spaced around a section of piping, for example at an axial position substantially centrally between the first and second excitation coils. Process 700 continues in block 707 with analyzing the decay profiles of the detected secondary magnetic fields to locate and evaluate a defect. As noted previously, the output signals detected by the magnetic fields can be indicative of a defect in the pipe due to effects on the eddy currents in the pipe. In particular, the decay profile can indicate the radial location (i.e., depth) of the defect. In some embodiments, the output signal can be used to determine both the axial location of a defect, as well as the radial location. As noted above, if the defect is on the external surface of the pipe, the loss is evident from the decay profile of the secondary magnetic field at an early stage. If the material loss is internal the dipole effect occurs later due to the time taken for the field to diffuse through the pipe wall. As a result, aberrations detected in the decaying output signal can be analyzed to determine the depth of any detected defect.

In some embodiments utilizing the pulsed transient eddy current technique, the apparatus is sufficiently sensitive to detect defects in the pipeline with a minimum size of 3T×3T×0.2T, where T is the nominal thickness of the pipe. In some embodiments, the apparatus is sufficiently sensitive to detect defects with a minimum size of 1T×1T×0.1T.

Figure 12:
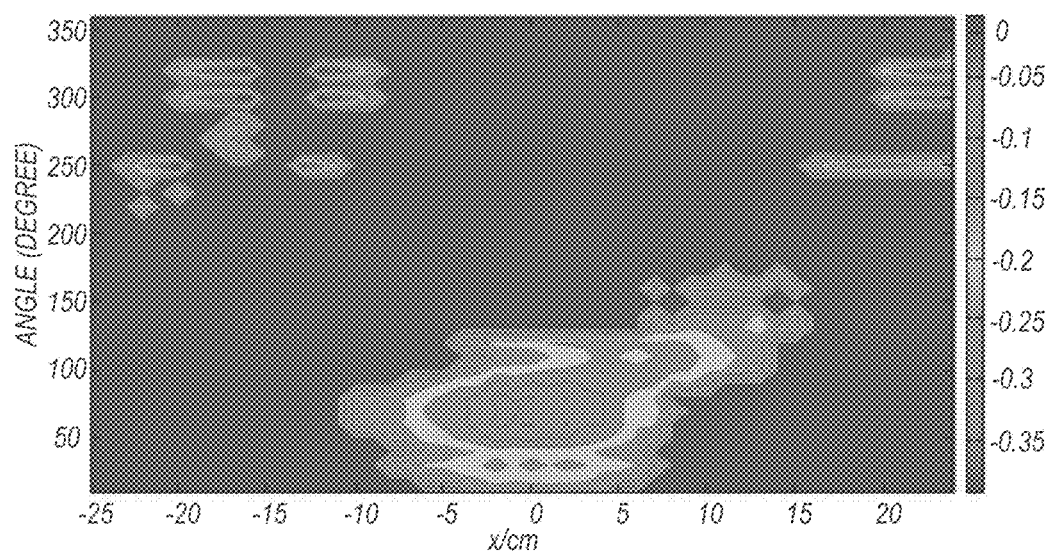
FIG. 12 illustrates a false-color graph of the detected secondary magnetic fields induced by the eddy currents.

As noted above, data representing the detected magnetic fields can be presented in a number of visual forms. FIG. 12 illustrates a false-color graph of the detected secondary magnetic fields induced by the eddy currents. As illustrated, the shading represents the magnetic field in units of microTesla as indicated on the vertical scale on the right of the diagram. The horizontal axis denotes the direction of the pipe and tool axis. The vertical axis denotes the angle in degrees of the sensor location measured, in this case, from the bottom of the pipe. The diminished magnetic field near the center of the pipe in the axial direction, and at approximately 75 degrees from the bottom of the pipe, indicates the location of a defect. Such a color-shaded graph can provide a simple and effective way to rapidly identify any defects in the pipe due to anomalous or irregular shading patterns. Various other such graphical or visual presentations of the magnetic field data can be utilized.

In some embodiments, a single apparatus may be configured for use either with AC current supplied to the excitation coils, as described above with respect to the embodiments of FIGS. 1-10, and/or with transient current supplied to the excitation coils, as described above with respect to FIG. 11. Such an apparatus may optionally include an electromagnetic yoke assembly comprising a plurality of electromagnets mounted about the piping. In use, the apparatus may be switched between an AC mode and a transient mode as desired. The use of both modes may improve accuracy and resolution in detecting flaws in the pipeline.

The previously described embodiments are described as having the magnetometers arranged around the circumference of the surface in a frame. In alternative embodiments, the magnetometers are arranged around the circumference of the surface in a plurality of frames. The plurality of frames may be disposed between the excitation coils. The frames may be positioned between the coils adjacent one another. The frames may also be evenly spaced between the coils in some embodiments. In some embodiments, the magnetometers of one frame may be angularly offset from the magnetometers of another frame.

The previously described embodiments of the technology have been shown and described as extending around the entire circumference of the pipe to be inspected. However, in alternative embodiments of the technology, the coils and magnetometers can extend over a portion less than the entire circumference. For example, although the particular embodiment illustrated in and described with reference to FIGS. 4 and 5 includes coils 202, 202' and magnetometers 106 that extend around the entire circumference of the pipe to be inspected, the coils and magnetometer may extend over a shorter arc along the surface to be inspected. For example, in some embodiments, the coils 202, 202' and the magnetometers 106 extend over half of the circumference of the pipe to be inspected. In other embodiments, the coils 202, 202' may extend over a greater or lesser portion of the surface than one-half of the circumference.

Moreover, arrangement of the coils and magnetometers are not limited to an arrangement along a concave arc to be positioned against the exterior of a curved surface. For example, the coils and the magnetometer may be arranged in a substantially planar arrangement. Such an embodiment may be advantageous for inspecting a substantially planar surface, of a curved surface having a relatively large diameter of curvature. The coils and the magnetometer may also be arranged along a convex arc to be positioned against the interior of a curved surface. Such an embodiment may be advantageous for inspecting an interior curvature of a curved surface.

The invention claimed is:

1. An apparatus for inspecting a section of piping, the apparatus comprising:
    an alternating current power source configured to generate an alternating current having a multi-frequency waveform synthesized from at least four different frequencies;
    a first excitation coil disposed at a first axial location, the first excitation coil being energized by the alternating current;
    a second excitation coil disposed at a second axial location, the second excitation coil being energized with the alternating current, wherein the first and second excitation coils are both energized by the alternating current such that the at least four different frequencies are applied simultaneously, the energized first and second excitation coils thereby inducing at least four different eddy currents in the section of piping that each corresponds to one of the at least four different frequencies;
a plurality of magnetometers disposed at an axial location between the first axial location and the second axial location, wherein the magnetometers are positioned to detect magnetic fields generated by the at least four eddy currents simultaneously; and
a data acquisition system operatively connected to receive output data from the plurality of magnetometers;
wherein the apparatus is movable axially along the section of piping.

2. The apparatus of claim 1, wherein the multi-frequency waveform generated by the second excitation coil is at a same polarity as the multi-frequency waveform generated by the first excitation coil.

3. The apparatus of claim 1, wherein the multi-frequency waveform generated by the second excitation coil is at an opposite polarity as the multi-frequency waveform generated by the first excitation coil.

4. The apparatus of claim 1, wherein the first excitation coil is disposed around the section of piping at the first axial location.

5. The apparatus of claim 1, wherein the plurality of magnetometers are circumferentially spaced around the section of piping at the axial location between the first and second axial locations.

6. The apparatus of claim 1, wherein the magnetometers comprise fluxgate magnetometers.

7. The apparatus of claim 1, wherein the magnetometers are located half way between the first excitation coil and the second excitation coil.

8. The apparatus of claim 1 wherein the magnetometers are disposed in a ring around the section of piping at an axial location between the first axial location and the second axial location.

9. The apparatus of claim 1, wherein the data acquisition system receives output data from the plurality of magnetometers wirelessly.

10. The apparatus of claim 1, further comprising means for detecting movement of the apparatus along the section of piping.

11. A method for examining a section of piping having a magnetically permeable pipe, the method comprising the steps:
placing a first excitation coil proximate said section of piping at a first axial location;
placing a plurality of magnetometers proximate said section of piping at a first distance from said first axial location, wherein said magnetometers are oriented toward said magnetically permeable pipe;
energizing said first excitation coil with an alternating current having a multi-frequency waveform synthesized from at least four different frequencies, wherein said first excitation coil is energized by the alternating current such that the at least four different frequencies are applied simultaneously, the energized first excitation coil thereby inducing at least four eddy currents in the section of piping that each corresponds to one of the at least four different frequencies;
monitoring said plurality of magnetometers and recording a plurality of signals therefrom to a data acquisition unit, wherein the plurality of magnetometers are configured to detect magnetic fields generated by each of the at least four eddy currents simultaneously and wherein the plurality of signals comprises signals corresponding to the detected magnetic fields; and
inferring from said plurality of signals a physical condition of said magnetically permeable pipe.

12. The method of claim 11, further comprising:
placing a second excitation coil proximate said section of piping opposite the plurality of magnetometers from the first excitation coil; and
energizing said second excitation coil simultaneously with energizing said first excitation coil and with the alternating current having the multi-frequency waveform synthesized from the at least four different frequencies, wherein said second excitation coils is energized by the alternating current such that the at least four different frequencies are applied to said second excitation coil simultaneously.

13. The method of claim 11, wherein said magnetometers are fluxgate magnetometers.

14. The method of claim 11, further comprising the step of moving said excitation coil and said plurality of magnetometers along said section of piping to a second position, and monitoring said plurality of magnetometers to receive a second plurality of signals therefrom.

15. The method of claim 11, wherein inferring from said plurality of signals a physical condition of said magnetically permeable pipe comprises determining an axial location of a defect.

16. The method of claim 11, wherein inferring from said plurality of signals a physical condition of said magnetically permeable pipe comprises determining a radial location of a defect.

17. The method of claim 11, wherein inferring from said plurality of signals a physical condition of said magnetically permeable pipe comprises determining an angular location of a defect.

18. A method for inspecting a section of a pipe, the method comprising:
placing a first excitation coil proximate said section at a first axial location;
placing a second excitation coil proximate said section at a second axial location axially spaced apart from said first axial location;
placing a plurality of magnetometers proximate said section at a third axial location between said first axial location and said second axial location, wherein said magnetometers are oriented toward said pipe;
energizing said first excitation coil with an alternating current having a multi-frequency waveform synthesized from at least four different frequencies;
energizing said second excitation coil with the alternating current, wherein the first and second excitation coils are both energized by the alternating current such that the at least four different frequencies are applied simultaneously, the energized first and second excitation coils thereby inducing at least four eddy currents in the section of piping that each corresponds to one of the at least four different frequencies;
recording a plurality of signals from the plurality of magnetometers to a data acquisition unit, wherein the plurality of magnetometers are configured to detect magnetic fields generated by the at least four eddy currents simultaneously and wherein said plurality of signals comprises signals corresponding to the detected magnetic fields; and determining, based at least in part on said plurality of signals, a location of a defect in said pipe.

19. The method of claim 18, wherein determining a location of said defect comprises determining an axial location of said defect.

20. The method of claim 18, wherein determining a location of said defect comprises determining a radial location of said defect.

21. The method of claim 18, wherein determining a location of said defect comprises determining an angular location of said defect.

22. The method of claim 18, wherein said defect is defined by a volume equal to or less than 3T×3T×0.2T, where T is the thickness of the pipe.

* * * * *